United States Patent [19]

Haugwitz et al.

[11] 4,145,431
[45] Mar. 20, 1979

[54] METHOD OF TREATING HELMINTHIASIS BY PARENTERAL ADMINISTRATION OF SULFIDE- AND SULFOXIDE-DERIVATIVES OF BENZIMIDAZOLES

[75] Inventors: Rudiger D. Haugwitz, Titusville; Larry R. Cruthers, Flemington, both of N.J.

[73] Assignee: E. R. Squibb & Sons, Inc., Princeton, N.J.

[21] Appl. No.: 878,498

[22] Filed: Feb. 16, 1978

[51] Int. Cl.$^2$ ............................................ A61K 31/415
[52] U.S. Cl. ................................. 424/273 B; 548/306
[58] Field of Search ......................... 424/273 R, 273 B; 548/306

[56] References Cited

U.S. PATENT DOCUMENTS

| 3,929,821 | 12/1975 | Beard et al. | 424/273 |
| 4,002,640 | 1/1977 | Beard et al. | 548/306 |

*Primary Examiner*—Sam Rosen
*Attorney, Agent, or Firm*—Lawrence S. Levinson; Merle J. Smith; Burton Rodney

[57] ABSTRACT

A method is provided for treating or inhibiting helminthiasis by parenterally or topically administering sulfide or sulfoxide derivatives of benzimidazoles having the structure

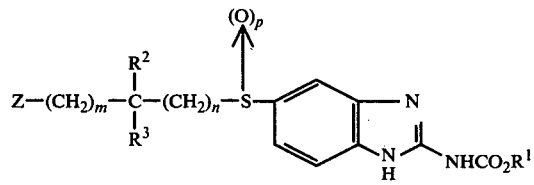

wherein $R^1$ is lower alkyl or phenyl-lower alkyl, $R^2$ and $R_3$ may be the same or different and are hydrogen or lower alkyl, Z is

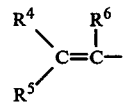

or $R^4-C\equiv C-$, $R^4$, $R^5$ and $R^6$ may be the same or different and are hydrogen, lower alkyl, or phenyl, and m is 0 to 3, n is 0 to 3, m + n being $\leq$ 5, and p is 0 or 1. Pharmaceutical compositions for use in the above method are also provided.

15 Claims, No Drawings

METHOD OF TREATING HELMINTHIASIS BY PARENTERAL ADMINISTRATION OF SULFIDE- AND SULFOXIDE-DERIVATIVES OF BENZIMIDAZOLES

BACKGROUND OF THE INVENTION

Various benzimidazole compounds are known for their use an anthelmintic agents. For example, U.S. Pat. No. 3,574,845 to Actor et al. and assigned to Smith Kline discloses 5(6)-benzene ring substituted benzimidazole-2-carbamate derivatives including 5(6)-methylthio-2-carboethoxyaminobenzimidazole and various 5(6)-alkyl-2-carbomethoxyaminobenzimidazoles.

U.S. Pat. Nos. 3,929,821 and 4,002,640 to Beard et al. and assigned to Syntex disclose various 5(6)-benzene ring substituted benzimidazole-2-carbamate derivatives including 5(6)-alkenylthio- and sulfinyl-2-carbomethoxyaminobenzimidazoles, as well as 5(6)-alkynyl thio- and sulfinyl-2-carbomethoxyaminobenzimidazoles, 5(6)-phenylsulfinyl-2-carbomethoxyaminobenzimidazole, 5(6)-cycloalkylsulfinyl-2-carbomethoxyaminobenzimidazoles and 5(6)-cyclopropylmethylsulfinyl-2-carbomethoxyaminobenzimidazole.

The benzimidazoles mentioned above are said to be active orally.

Other benzimidazoles useful as anthelmintic agents are disclosed in U.S. Pat. Nos. 3,929,822, 3,929,823 3,929,824, 3,935,209, 3,965,113 and 4,005,202 all Beard et al. and assigned to Syntex; U.S. Pat. Nos. 3,682,952 to Actor et al, 3,578,676 and 3,694,455 to Dunn, 3,915,986 and 3,969,526 to Gyurik, all assigned to Smith Kline; and U.S. Pat. No. 3,738,993 to Haugwitz et al. assigned to Squibb.

The aforementioned patents teach that the benzimidazole compounds disclosed therein are useful orally in treating helminthiasis.

U.S. Pat. Nos. 3,954,791 to Loewe et al. and 3,928,375 to Duwel et al., both assigned to Hoechst disclose 2-carbalkoxy-amino-benzimidazole-5(6)-phenyl and phenylthio ethers which are said to be active perorally and subcutaneously.

In accordance with the present invention, it is indeed surprising that 5(6)-lower alkenyl or lower alkynyl thio or sulfinyl-2-carbomethoxyaminobenzimidazoles may be effectively administered parenterally in the treatment or prevention of helminthiasis inasmuch as most benzimidazole compounds are active only upon oral administration.

DESCRIPTION OF THE INVENTION

The present invention relates to a method for treating or inhibiting helminthiasis by parenterally or topically administering to a mammalian host a sulfide or sulfoxide derivative of a benzimidazole having the structure

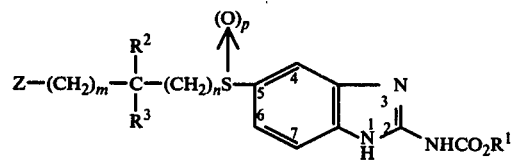

wherein $R^1$ is lower alkyl or phenyl-lower alkyl, $R^2$ and $R^3$ may be the same or different and are hydrogen or lower alkyl, Z is

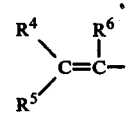

or $R^4$—C≡C—, $R^4$, $R^5$ and $R^6$ may be the same or different and may be hydrogen, lower alkoxy, or phenyl, m is 0 to 3, n is 0 to 3 and m + n is ≦ 5 and p is 0 or 1.

The term "lower alkyl" as used herein includes straight or branched chain aliphatic hydrocarbon radicals having up to and including seven carbon atoms, such as methyl, ethyl, propyl, isopropyl, n-butyl, isobutyl, t-butyl, amyl, hexyl, heptyl and the like.

$(CH_2)_m$ and $(CH_2)_n$ represent a single bond or straight or branched chain alkylene radicals containing 3 or less carbons in the longest normal chain.

Accordingly the compounds of the invention may have the following structures:

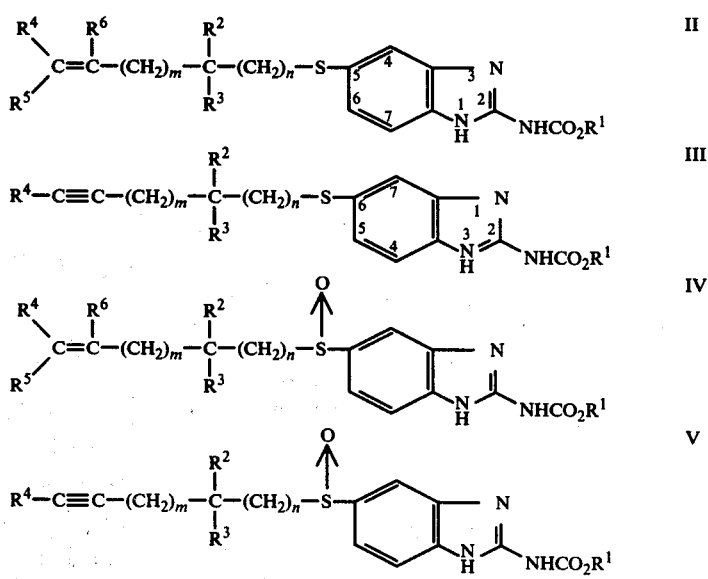

The 5-thiobenzimidazole derivatives of structures II and IV may be prepared by reaction of nitro-activated halobenzenes of structure VI

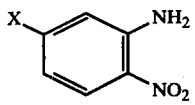
VI wherein X is Cl or Br, with a mercaptan derivative of structure VII

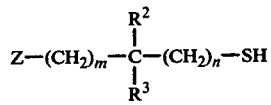
VII by heating compounds VI and VII is solvents such as methanol, ethanol or acetonitrile at elevated temperatures ranging from about 50 to about 150° C. for one to twenty-four hours in the presence of alkali hydroxides, carbonates or alkoxides, such as sodium or potassium hydroxide, sodium or potassium carbonate or sodium or potassium methoxide, to form the aniline VIII.

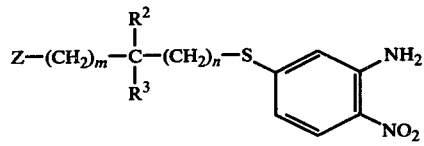
VIII

Compound VIII is reduced (SnCl$_2$; Fe), preferably with activated iron (Sandler and Karo, "Organic Functional Group Preparations," 1968, pp 339–340). Thus, refluxing the compound of structure VIII in benzene together with activated iron for several hours, preferably four to ten hours, and adding small quantities of water to the reaction mixture during the course of reflux yields the diamine IX, which because of its susceptibility to air, is stored under nitrogen.

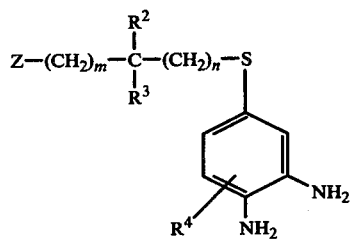
IX

The thiobenzimidazole derivatives of structure I, II or III is achieved by ring closure of compound IX which may be carried out in various ways. Whereas refluxing of the o-phenylenediamine IX with the isolated thiourea derivative X in alcohols such as methanol or ethanol will furnish compounds of structure I, II or III, the preferred method of preparing I, II or III is by forming X in situ (react 2-methyl-2-thiopseudourea with a chloroformate

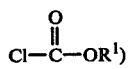

and then without isolating it, adding the o-phenylenediamine IX and refluxing it for periods of thirty minutes to five hours to yield the sulfide product of structure I, II or III

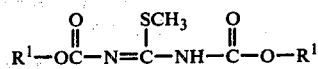
X

The sulfide compound of structure II or III may be oxidized to the corresponding sulfoxide IV or V employing one equivalent of an oxidizing agent such as hydrogen peroxide in acetic acid, sodium meta periodate or m-chloroperbenzoic acid.

Compounds of structures IV and V may also be prepared by oxidizing the formula VIII 2-nitroaniline derivative with one equivalent of oxidizing agent to form a sulfinyl-2-nitroaniline XI which is then reduced to the sulfinyl o-phenylenediamine XII

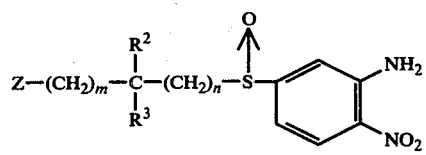
XI

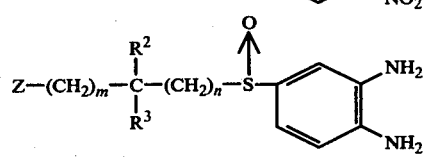
XII

The sulfinyl o-phenylenediamine XII is then reacted with the thiourea X in the presence of an alcohol solvent (ROH) or other non-reacting solvent to form the benzimidazole sulfoxide of structure IV or V.

The starting materials employed in the above reactions are either known in the art or easily prepared according to conventional techniques. Thus, for example, the nitro-activated halobenzenes of formula VI may be prepared by the following reaction sequence:

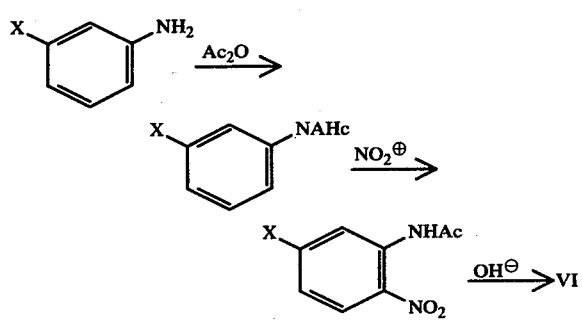

The benzimidazole derivatives of structure I may also be prepared as described in U.S. Pat. Nos. 3,929,821 and 4,002,640 to Beard et al.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

In accordance with the present invention, the compounds of formula I are administered parenterally, such as subcutaneously, intravenously, intramuscularly or interperitoneally, or topically (cutaneously), preferably directly on to exposed skin surface, to a mammalian host in the treatment and/or prevention of helminthiasis. Helminthiasis is a parasitic disease which causes widespread and often serious infection in domesticated animals, such as swine, horses, cattle, dogs, cats and sheep. The compounds administered parenterally or topically are useful in treating infections caused by Haemonchus, Ostertagia, Trichostrongylus, Cooperia, Dictyocaulus, Nematodirus, Bunostomum, Strongyloides, Oesophagostomum, Trichuris, and liver flukes.

In preparing injectable compositions, the compounds are mixed with a non-toxic, physiologically acceptable non-pyrogenic carrier such as sterile water, sterile saline solution, benzyl benzoate, 1,3-butylene glycol, ethyl oleate, castor oil, glyceryl triacetate, sesame oil, and sesame oil:benzyl benzoate (1:1). The parenteral product will usually take the form of a suspension containing from about 1 to about 10% by weight of the compound of formula I.

The above injectable compositions may also include a non-toxic physiologically acceptable non-pyrogenic suspending agent. Thus, where a non-oily carrier is employed such as water, suspending agents such as carboxymethyl cellulose, methyl cellulose, polyvinyl pyrrolidone or non-antigenic gelatin may be employed. Where the carrier employed is an oil, aluminum monostearate may be employed as a suspending agent. The suspending agent may be employed in amounts ranging from about 0.05 to about 2%, and preferably from about 0.1 to about 1% by volume of carrier (the above % may be based on the weight of the carrier where the carrier is qs to 100g).

A non-toxic, non-pyrogenic wetting agent may also be included in the injectable compositions in amounts ranging from about 0.005 to about 0.2% and preferably from about 0.01 to about 0.1% by weight of the carrier. Examples of suitable wetting agents include non-ionic surfactants such as polyoxyethylene sorbitan monostearate, polyoxyethylene sorbitan monooleate [e.g., Tweens] and fatty acid monoglycerides or diglycerides. Other surfactants suitable for use herein are disclosed in the published literature, for example, Kirk-Othmer, Encyclopedia of Chemical Technology, Second Edition, Volume 19, page 507 et seq.

In preparing topical or cutaneous compositions, the anthelmintic compounds are mixed with carriers which are effective in penetrating the skin, whereby the compounds are absorbed by the animal through the skin and transmitted systemically within the animal. A wide range of appropriate carriers may be employed to pass the compound through the skin. The composition employed may be a cream. A liquid composition, however, is particularly convenient to use, e.g., facilitating measuring out doses, and facilitating absorbance through the skin. Thus, a solution or suspension of the compound in a liquid carrier is preferred. Solutions are especially good for transmitting the compound through the skin and are therefore most preferred. The liquid carrier preferably comprises one or more liquids selected from hydrocarbons (e.g., aromatic hydrocarbons, such as an aromatic hydrocarbon fraction of boiling point 130°-250° C., e.g., 180°-220° C., xylene, benzene or toluene, or paraffins, such as those of 6-20 carbon atoms), halogenated aliphatic hydrocarbons (e.g., carbon tetrachloride), ketones (e.g., cyclohexanone or 2-butanone), esters (e.g., ethyl acetate, ethyl benzoate or triacetin), ethers (e.g., diisopropyl ether or tetrahydrofuran), alcohols (e.g., alkanols of 2-8 carbon atoms, such as butyl alcohol, amyl alcohol or isopropyl alcohol, or glycols, such as monopropylene glycol), amides (e.g., dimethylformamide), sulphones (e.g., dimethyl sulphone or sulpholane) and sulphoxides (e.g., dimethyl sulphoxide). In many cases a mixture of liquids is desirable. Preferably the liquid carrier comprises one or more liquids selected from hydrocarbons (e.g., aromatic hydrocarbons especially xylene), alcohols (e.g., isopropyl alcohol or amyl alcohol) and sulphoxides (e.g., dimethyl sulphoxide). Water tends to be ineffective as a liquid carrier for passing the compound through the skin of the animal. Accordingly, the carrier in the liquid compositions preferably comprises an organic liquid.

The viscosity of liquid compositions may be increased over what it would otherwise be by including thickeners which increase the viscosity. This may be desirable in order to retard or prevent the composition from running off the animal.

The additives may include, for example, a surface active agent, an animal fat or wax, e.g., lanolin, a mineral oil, e.g., liquid paraffin, a vegetable oil, e.g., peanut oil, olive oil, corn oil or caster oil, or a polymer, e.g., a hydrocarbon polymer such as polyisobutene.

The surface active agents may comprise anionic compounds for example, soaps, fatty sulphate esters, such as dodecyl sodium sulphate, fatty aromatic sulphonates such as alkylbenzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic surface active agents such as for example condensation products of fatty acids, fatty alcohols or fatty polyhydric alcohols, or the products obtained from the latter by condensation with ethylene oxide, or the products known as block copolymers of ethylene oxide and propylene oxide. The surface active agents may also comprise cationic agents such as, for example, cetyl trimethylammonium bromide.

The term "surface active agent" is used in the broad sense to cover materials variously called wetting agents, emulsifying agents and dispersing agents.

The composition may contain substances whose taste deters other animals from licking the composition off the animal treated. An example of such a substance is bitter aloes.

Generally, additives facilitating the use in pour-on formulations of other materials, e.g., systemic insecticides, active on animal physiology may be of use also in the present composition.

In general, in carrying out the method of the invention, the parenteral or topical composition described above will be administered to animals in a single dose to provide from about 1 to about 100 mg active compound per kilogram of animal body weight. It is preferred to employ in the range of 2.5-25 mg per kilogram of body weight. The compounds may be divided into a plurality of smaller doses given over one or more days, for example, up to 14 days.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

[5-(2-Propenylthio)-1H-benzimidazol-2-yl]carbamic acid, methyl ester

A. 2-Nitro-5-(2-propenylthio)aniline

To a solution of 7 g of 2-nitro-5-chloroaniline in 200 ml of absolute ethanol there is added 4.2 of allyl mercaptan and 2.5 g of Na-methoxide. Then the mixture is refluxed for three hours, the solvent is evaporated and the residue is chromatographed on neutral alumina (Activity IV). Elution with ether-petroleum ether yields 4.6 g of 2-nitro-5-(2-propenylthio)aniline.

B. 4-(2-Propenylthio)-o-phenylenediamine

To a solution of 4 g of 2-nitro-5-(2-propenylthio)aniline in 200 ml of benzene there is added 4.0 g of activated iron (Sandler and Karo, *Organic Functional Group Preparations,* Vol. 1, 1968, pp. 339–340), and the mixture is refluxed for three hours. During the reflux period, water is added in small portions every 15 minutes until a total of 20 ml is reached. The solvent is decanted. The iron sludge is extracted with hot benzene and the combined dried benzene fractions are evaporated in vacuo. The resulting residue is stored under nitrogen at 0°.

C. [5-(2-Propenylthio)-1H-benzimidazol-2-yl]carbamic acid, methyl ester

To a mixture of 5.7 g of 2-methyl-2-thiopseudourea sulfate in 3.4 ml of water there is added at 0° 3.6 ml of methyl chloroformate. The mixture is stirred for 10 minutes at this temperature. Then, there is added dropwise 7.6 ml of 25% NaOH. The temperature is kept below 25° and the mixture is stirred for 10 minutes. Then, 3.8 ml of acetic acid is added and again the temperature is kept below 25°. After a stirring period of 10 minutes, there is added the total of 4-(2-propenylthio)-o-phenylenediamine from Example 1B dissolved in 10 ml of methanol and the mixture is refluxed for one hour. The resulting solid is filtered off, washed with water and dried to yield 4 g. Crystallization from acetonitrile furnishes the analytically pure title compound, m.p. 197°–198°.

EXAMPLE 2

[5-(2-Propenylsulfinyl)-1H-benzimidazol-2-yl]carbamic acid, methyl ester

To an ice-cold solution of 40 mmol of [5-(2-propenylthio)-1H-benzimidazol-2-yl]carbamic acid, methyl ester prepared as described in Example 1, in 150 ml methanol is added 8.98 g (42 mmol) sodium metaperiodate in 150 ml water. The resulting suspension is stirred at 5° C. for 24 hours, then partitioned between water and dichloromethane. The layers are separated and the aqueous layer re-extracted. The organic layers are combined and washed with saturated NaCl, dried, filtered and evaporated to yield a residue which is crystallized three times from acetonitrile to yield the title sulfinyl compound.

EXAMPLE 3

[5-(2-Methyl-2-propenylthio)-1H-benzimidazole-2-yl]carbamic acid, methyl ester

Following the procedure of Example 1 and substituting isobutenylmercaptan [$CH_2$=$C(CH_3)$—$CH_2SH$] for allyl mercaptan, the title compound is obtained.

EXAMPLE 4

[5-(2-Methyl-2-propenylsulfinyl)-1H-benzimidazol-2-yl]carbamic acid, methyl ester Following the procedure of Example 2, except employing the benzimidazole of Example 3, the title compound is obtained.

EXAMPLE 5

[5-(2-Butenylthio)-1H-benzimidazol-2-yl]carbamic acid, ethyl ester

Following the procedure of Example 1 and substituting crotyl mercaptan for allyl mercaptan and substituting ethyl chloroformate for methyl chloroformate in Example 1, the title compound is obtained.

EXAMPLE 6

[5-(2-Butenylsulfinyl)-1H-benzimidazol-2-yl]carbamic acid, ethyl ester

Following the procedure of Example 2, except substituting the benzimidazole of Example 5, the title compound is obtained.

EXAMPLE 7

[5-(2-propenylsulfinyl)-1H-benzimidazol-2-yl]carbamic acid, methyl ester

A. 2-Nitro-5-(2-propenylthio)aniline

To a solution of 7 g of 2-nitro-5-chloroaniline in 200 ml of absolute ethanol there is added 4.2 g of allyl mercaptan and 2.5 g of Na-methoxide. Then the mixture is refluxed for three hours, the solvent is evaporated and the residue is chromatographed on neutral alumina (Activity IV). Elution with ether-petroleum ether yields 4.6 g of 2-nitro-5(2-propenylthio)aniline.

B. 2-Nitro-5-(2-propenylsulfinyl)aniline

To a solution of 0.01 mole of the above aniline in 50 ml of methanol under $N_2$ there is added a solution of 2.2 g $NaIO_4$ in 20 ml of water at 0°–5° C. for 30 hours. The mixture is extracted with dichloromethane and the combined, dried organic layers are evaporated to yield the above sulfoxide.

C. 5-(2-Propenylsulfinyl)-o-phenylenediamine

To a suspension of 0.0075 mole of 2-nitro-5-(2-propenylsulfinyl)aniline in 75 ml of absolute ethanol under $N_2$ there is added a solution of 4.9 g of $Na_2S_2O_4$, 4.9 ml of concentrated $NH_3$ and 30 ml of water. The mixture is refluxed for 15 minutes and an additional 0.4 g of $Na_2S_2O_4$ is added. After 15 minutes of reflux the ethanol is evaporated. The aqueous residue is made basic (pH 12) and extracted with dichloromethane. The combined, dried extracts are evaporated and the resulting oily residue is used immediately in the next reaction.

D. [5-(2-Propenylsulfinyl)-1H-benzimidazol-2-yl]carbamic acid, methyl ester

To a solution of the above diamine in 25 ml of methanol there is added 0.5 ml of acetic acid and 1.5 g of 1,3-bis(methoxycarbonyl)-S-methylisothiourea. The mixture is refluxed for 3 hours. The methanol is evaporated and water is added. The resulting solid is filtered off and crystallized from acetonitrile to yield the title compound.

EXAMPLE 8

[5-(2-Propinylsulfinyl)-1H-benzimidazol-2-yl]carbamic acid, methyl ester

Following the procedure of Example 1 but substituting for 2-nitro-5-(2-propenylthio)aniline, 2-nitro-5-(2-propinylthio)aniline, the title compound is obtained.

EXAMPLE 9

Parenteral Formulation of [5-(propenylthio)-1H-benzimidazol-2-yl]carbamic acid, methyl ester A suspension suitable for subcutaneous administration is prepared by dispersing 150 mg of [5-(propenylthio)-1H-benzimidazol-2-yl]carbamic acid, methyl ester in about 10 ml of water for injection, USP. The resulting suspension contains 1.5% by weight of the benzimidazole compound.

EXAMPLE 10

Testing of Parenteral Formulation of [5-(propenylthio)-1H-benzimidazol-2-yl]carbamic acid, methyl ester The following test is carried out to determine the effectiveness of treating sheep infected with gastrointestinal nematodes by subcutaneously administering a single dose of an aqueous suspension of [5-(propenylthio)-1H-benzimidazol-2-yl]carbamic acid, methyl ester prepared in Example 1 so as to inject 10 mg of the above benzimidazole compound per kg of body weight of the test animal.

Egg per gram of feces (EPG) counts are conducted 2-4 days (avg. 3) prior to subcutaneously administering the above benzimidazole compound in order to determine the degree of parasitism of the test animal. Generally, animals are used which have at least 10,000 eggs per gram of feces although, on occasion, lambs with 8-9,000 eggs per gram can be used. An average pretreatment EPG is calculated for the test animal and medication is given according to individual body weight (10 mg/kg).

EPG's are conducted daily during the week the animal is on test and the final three (3) EPG's are used to calculate an average post-treatment EPG. The percent reduction in the EPG count for a given compound is calculated by taking the average pretreatment EPG and dividing this figure into the average post-treatment EPG and substracting the quotient from 100.

The [5-(propenylthio)-1H-benzimidazol-2-yl]-carbamic acid, methyl ester in the form of an aqueous suspension is found to be extremely effective in reducing the fecal egg count (EPG) when administered subcutaneously at 10 mg/kg.

EXAMPLE 11

A. Dermal Formulation of [5-(propenylthio)-1H-benzimidazol-2-yl]carbamic acid, methyl ester A solution for cutaneous administration is prepared by dissolving 327 mg of [5-(propenylthio)-1H-benzimidazol-2-yl]carbamic acid, methyl ester in a solution of about 4cc xylene and 1 cc dimethyl sulfoxide.

B. Testing of Dermal Formulation of [5-(propenylthio)-1H-benzimidazol-2-yl]carbamic acid, methyl ester In a manner similar to that described in Example 9, the composition of Example 11A is tested to determine the effectiveness of treating sheep infected with gastrointestinal nematodes by cutaneously administering (by syringe directly onto a shaven exposed skin surface) a single dose of the above solution of [5-(propenylthio)-1H-benzimidazol-2-yl]carbamic acid, methyl ester so as to provide 10 mg of the above benzimidazole compound per kg of body weight of the test animal.

The Example 11A topical formulation is found to be extremely effective in reducing the fecal egg count (EPG), when administered cutaneously at 10 mg/kg.

EXAMPLES 12 to 17

Parenteral Formulations of Compounds of Examples 2 to 6 and 8

Following the procedure of Example 9, parenteral formulations are prepared for the compounds of Examples 2 to 6 and 8.

EXAMPLES 18 to 23

Testing of Parenteral Formulations of Examples 12 to 17

Following the procedure of Example 10, the parenteral formulations of Examples 12 to 17 are tested and are found to be effective in reducing fecal egg count.

What is claimed is:

1. A method of treating helminthiasis, which comprises parenterally administering to a mammalian host an effective amount of a compound of the structure

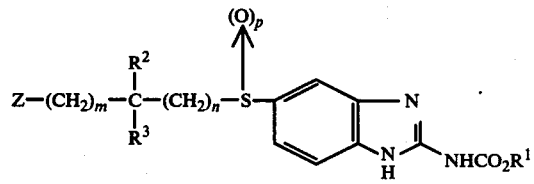

wherein $R^1$ is lower alkyl, phenyl-lower alkyl, $R^2$ and $R^3$ are the same or different and are selected from the group consisting of hydrogen and lower alkyl, Z is

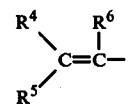

or $R^4$—C≡C— and $R^4$, $R^5$ and $R^6$ may be the same or different and are selected from the group consisting of hydrogen, lower alkyl and phenyl, m is 0 to 3, n is 0 to 3 and m + n is ≦ 5 and p is 0 or 1, dispersed in a nontoxic non-pyrogenic physiologically acceptable carrier.

2. The method as defined in claim 1 wherein said compound has the formula

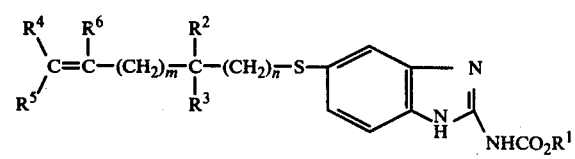

3. The method as defined in claim 1 wherein said compound has the formula

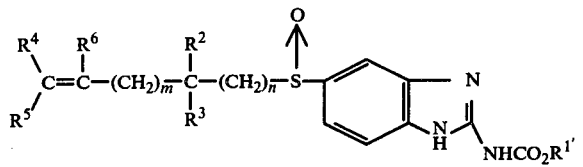

4. The method as defined in claim 1 wherein said compound has the formula

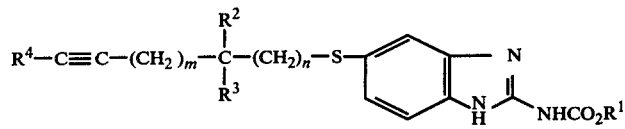

5. The method as defined in claim 1 wherein said compound has the formula

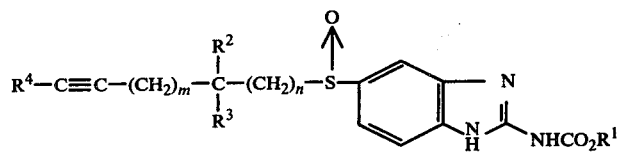

6. The method as defined in claim 1 where in said compound $R^1$ is lower alkyl or benzyl.

7. The method as defined in claim 1 where in said compound $R^2$ and $R^3$ are hydrogen or methyl.

8. The method as defined in claim 1 where in said compound $R^4$ and $R^5$ are hydrogen.

9. The method as defined in claim 1 where in said compound m is 0 and n is 0, and $R^2$ and $R^3$ are hydrogen.

10. The method as defined in claim 1 wherein said compound has the name [5-(2-propenylsulfinyl)-1H-benzimidazol-2-yl]carbamic acid, methyl ester.

11. The method as defined in claim 1 wherein said compound has the name [5-(2-propinylsulfinyl)-1H-benzimidazol-2-yl]carbamic acid, methyl ester.

12. The method as defined in claim 1 wherein said compound is administered subcutaneously.

13. The method as defined in claim 1 wherein said compound is administered intravenously.

14. An injectable composition for use in treating helminthiasis in mammalian species comprising an effective amount of a compound of the structure

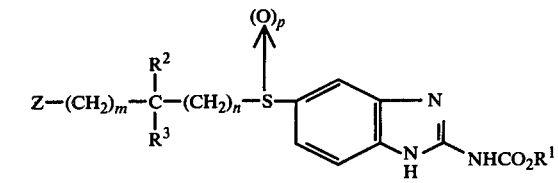

wherein $R^1$ is lower alkyl, phenyl-lower alkyl, $R^2$ and $R^3$ are the same or different and are selected from the group consisting of hydrogen and lower alkyl, Z is

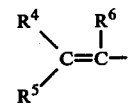

or $R^4$—C≡C— and $R^4$, $R^5$ and $R^6$ may be the same or different and are selected from the group consisting of hydrogen, lower alkyl and phenyl, m is 0 to 3, n is 0 to 3 and m + n is ≦ 5 and p is 0 or 1 and a non-toxic non-pyrogenic physiologically acceptable carrier therefor selected from the group consisting of benzyl benzoate, 1,3-butylene glycol, ethyl oleate, glyceryl triacetate, mixtures thereof, a mixture of benzyl benzoate and sesame oil, and sterile water for injection.

15. The composition as defined in claim 14 wherein said compound has the name [5-(2-propenylsulfinyl)-1H-benzimidazol-2-yl]carbamic acid, methyl ester.

* * * * *

UNITED STATES PATENT AND TRADEMARK OFFICE
CERTIFICATE OF CORRECTION

PATENT NO. : 4,145,431

DATED : March 20, 1979

INVENTOR(S) : Rudiger D. Haugwitz et al.

It is certified that error appears in the above-identified patent and that said Letters Patent are hereby corrected as shown below:

Column 2, next to the first structure insert --I--.
Column 4, line 45, in the second structure of the reaction sequence, "-NAHc" should read -- -NHAc --.
Column 11, in the structure of Claim 3, "-NHCO$_2$R$^1$'" should read -- -NHCO$_2$R$^1$ --.

Signed and Sealed this

Twelfth Day of June 1979

[SEAL]

Attest:

RUTH C. MASON
Attesting Officer

DONALD W. BANNER
Commissioner of Patents and Trademarks